(12) United States Patent
Zhou

(10) Patent No.: US 7,835,117 B2
(45) Date of Patent: Nov. 16, 2010

(54) DETECTION OF MAGNETIC BEADS USING A MAGNETORESISTIVE DEVICE TOGETHER WITH FERROMAGNETIC RESONANCE

(75) Inventor: Yuchen Zhou, Milpitas, CA (US)

(73) Assignee: Headway Technologies, Inc., Milpitas, CA (US)

( * ) Notice: Subject to any disclaimer, the term of this patent is extended or adjusted under 35 U.S.C. 154(b) by 0 days.

(21) Appl. No.: 12/800,323

(22) Filed: May 12, 2010

(65) Prior Publication Data

US 2010/0232075 A1    Sep. 16, 2010

Related U.S. Application Data

(62) Division of application No. 11/528,878, filed on Sep. 28, 2006, now Pat. No. 7,729,093.

(51) Int. Cl.
  *G11B 5/127*   (2006.01)
(52) U.S. Cl. ............................................. 360/324.11
(58) Field of Classification Search ........... 360/327.22, 360/324.11, 327.31, 327.1; 29/603.14, 603.08
See application file for complete search history.

(56) References Cited

U.S. PATENT DOCUMENTS

| | | | |
|---|---|---|---|
| 5,768,240 A * | 6/1998 | Hiraga ........................... | 720/656 |
| 5,841,744 A * | 11/1998 | Menke et al. ............ | 369/30.85 |
| 5,981,297 A | 11/1999 | Baselt | |
| 6,518,747 B2 | 2/2003 | Sager et al. | |
| 6,743,639 B1 | 6/2004 | Tondra et al. | |
| 6,744,704 B1 * | 6/2004 | Funaya et al. ............ | 369/30.85 |
| 6,875,621 B2 | 4/2005 | Tondra | |
| 2006/0020371 A1 | 1/2006 | Ham et al. | |
| 2008/0221432 A1 * | 9/2008 | Zhou ......................... | 600/420 |

OTHER PUBLICATIONS

"A biosensor based on magnetoresistance technology," by David R. Baselt et al., Biosensors & Bioelectronics 13 (1998) pp. 731-739.
"Ferromagnetic resonance of monodisperse Co particles," by U. Wiedwald et al., J. Vac. Sci. Technol. A 19(4), Jul./Aug. 2001, pp. 1773-1776, 2001 American Vacuum Society.
"Superparamagnetism and Transverse Susceptibility in Magnetic Nanoparticle Systems," by L. Spinu et al., IEEE Transactions on Magnetics, vol. 36, No. 5, Sep. 2000, pp. 3032-3034.
"Analytical and Micromagnetic Modeling for Detection of a Single Magnetic Microbead or Nanobead by Spin Valve Sensors," by Guanxiong Li et al., IEEE Transactions on Magnetics, vol. 39, No. 5, Sep. 2003, pp. 3313-3315.

(Continued)

*Primary Examiner*—Allen T Cao
(74) *Attorney, Agent, or Firm*—Salle Ackerman LLC; Stephen B. Ackerman

(57) ABSTRACT

A method and apparatus for detecting the presence of magnetic beads is disclosed. By providing both a static magnetic field and a magnetic field that alternates in the MHz range, or beyond, the bead can be excited into FMR (ferromagnetic resonance). The appearance of the latter is then detected by a magneto-resistive type of sensor. This approach offers several advantages over prior art methods in which the magnetic moment of the bead is detected directly.

22 Claims, 13 Drawing Sheets

OTHER PUBLICATIONS

"Model and Experiment of Detecting Multiple Magnetic Nanoparticles as Biomolecular Labels by Spin Valve Sensors," by Guanxiong Li et al., IEEE Transactions on Magnetics, vol. 40, No. 4, Jul. 2004, pp. 3000-3002.

"The BARC biosensor applied to the detection of biological warfare agents," by R.L. Edelstein et al., Biosensors & Bioelectronics 14 (2000) pp. 805-813.

"Towards a magnetic microarray for sensitive diagnostics," by Shan X. Wang et al., Journal of Magnetism and Magnetic Materials 293, (2005), pp. 731-736.

"A DNA array sensor utilizing magnetic microbeads and magnetoelectronic detection," by M.M. Miller et al., Journal of Magnetism and Magnetic Materials 225 (2001), pp. 138-144.

"Detection of single micron-sized magnetic bead and magnetic nanoparticles using spin valve sensors for biological applications," by Guanxion Li et al., Journal of Applied Physics, vol. 93, No. 10, May 15, 2003, pp. 7557-7559.

"Biodetection using magnetically labeled biomolecules and arrays of spin valve sensors (invited)," by H.A. Ferreira et al., Journal of Applied Physics, vol. 93, No. 10, May 15, 2003, pp. 7281-7286.

"Single magnetic microsphere placement and detection on-chip using current line designs with integrated spin valve sensors: Biotechnological applications," Journal of Applied Physics, vol. 91, No. 10, May 15, 2002, pp. 7786-7788.

Ferromagnetic resonance in periodic particle arrays, by S. Jung et al., Physical Review B 66, 132401 (2002), pp. 1-4.

Ferromagnetic resonance in a suspension of single-domain particles, by Yuri L. Raikher et al., Physical Review B, vol. 50, No. 9, Sep. 1, 1994, pp. 6250-6259.

"Thermally excited ferromagnetic resonance as diagnostic tool for spin valve heads," by Yuchen Zhou et al., Journal of Applied Physics, vol. 93, No. 10, May 15, 2003, pp. 8579-8591.

"Ferromagnetic resonance in ferrite nanoparticles with uniaxial surface anisotropy," by V.P. Shilov et al., Journal of Applied Physics, vol. 85, No. 9, May 1, 1999, pp. 6642-6647.

"Stochastic resonance and phase shofts in superparamagnetic particles," by Yuri L. Raikher et al., Physical Review B, vol. 54, No. 5, Aug. 1, 1995, pp. 3493-3498.

"Ferromagnetic resonance evidence for superparamagnetism in a partially crystallized metallic glass," by R.S. De Biasi et al., Physical B, vol. 42, No. 1, Jul. 1, 1990, pp. 527-529.

"High-frequency ferromagnetic resonance on ultrafine cobalt particles," by M. Respaud et al., Physical Review B, vol. 59, No. 6, Feb. 1, 1999, pp. R3934-R3937.

"Micromagnetic calculations of ferromagnetic resonance in submicron ferromagnetic particles," by S. Jung et al., Physical Review B 66, 132405, (2002), pp. 1-4.

"In situ detection of single micron-sized magnetic beads using magnetic tunnel junction sensors," by Weifeng Shen et al., Applied Physics Letters 86, 253901 (2005), pp. 1-3.

"Effect of spin-valve sensor magnetostatic fields on nanobead detection for biochip applications," by H.A. Ferreira et al., Journal of Applied Physics 97, 10Q904 (2005), pp. 1-3.

"Effective-susceptibility tensor for a composite with ferromagnetic inclusions: Enhancement of effective-media theory and alternative ferromagnetic approach," by V.B. Bregar et al., Journal of Applied Physics, vol. 95, No. 11, Jun. 1, 2004, pp. 6289-6293.

Microwave Ferrites and Ferrimagnetics, by Benjamin Lax, Ph.D et al., Lincoln Laboratory Publications, McGraw-Hill Book Company, Inc. New York, Copyright 1962, Chapter 4, Ferromagetic Resonance, pp. 145-151.

Ferromagnetic Resonance, The Phenomenon of Resonant Absorption of a High-Frequency Magnetic Field in Ferromagnetic Substances, by S. V. Vonsovskii, Pergamon Press, New York, Copyright 1966, pp. 18-19 and 40-47.

* cited by examiner

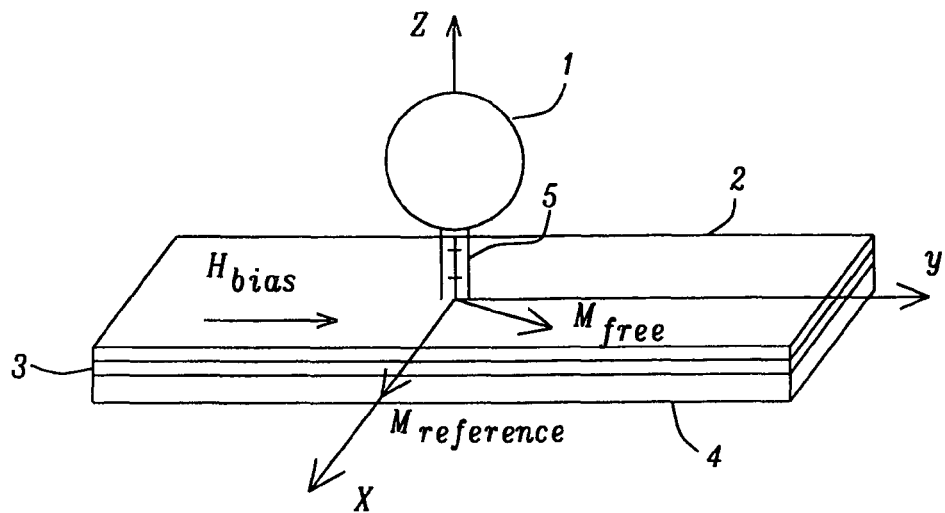
FIG. 1 - Prior Art
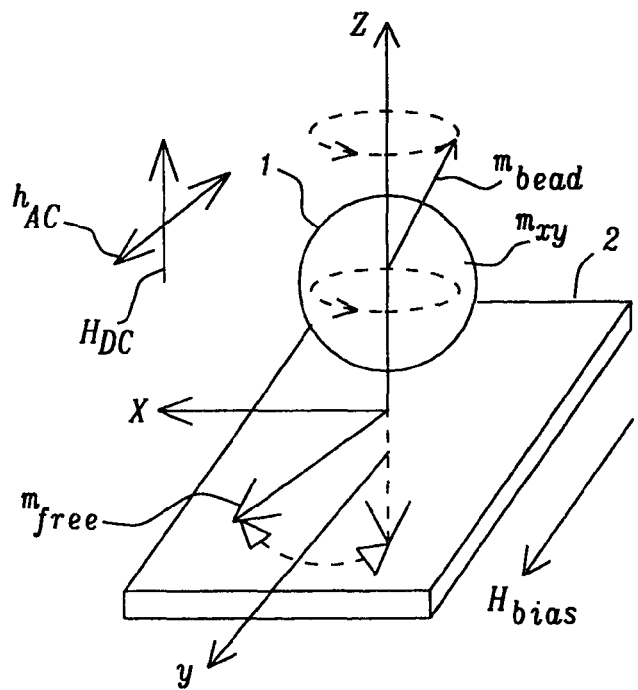
FIG. 2

Viewed along y axis direction

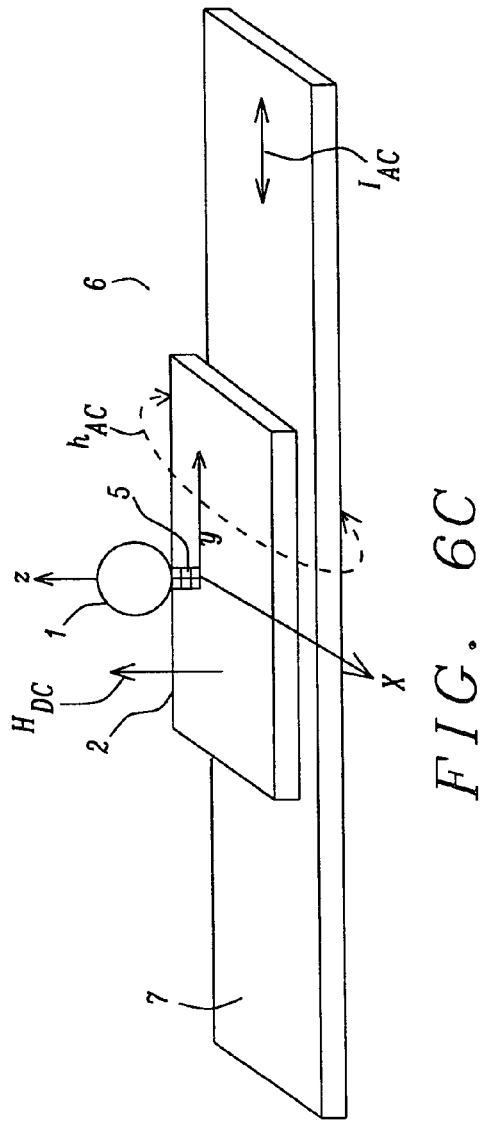
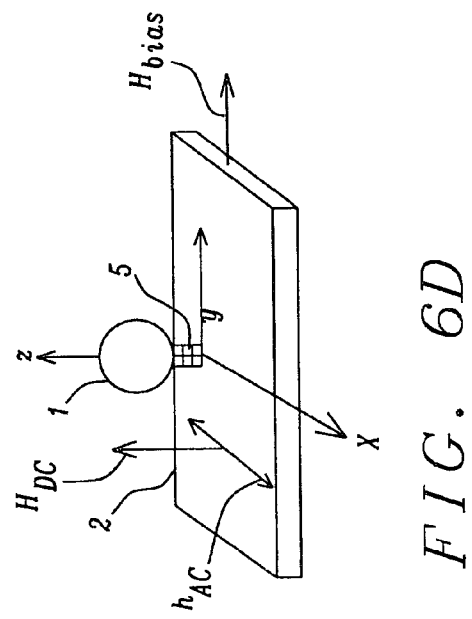

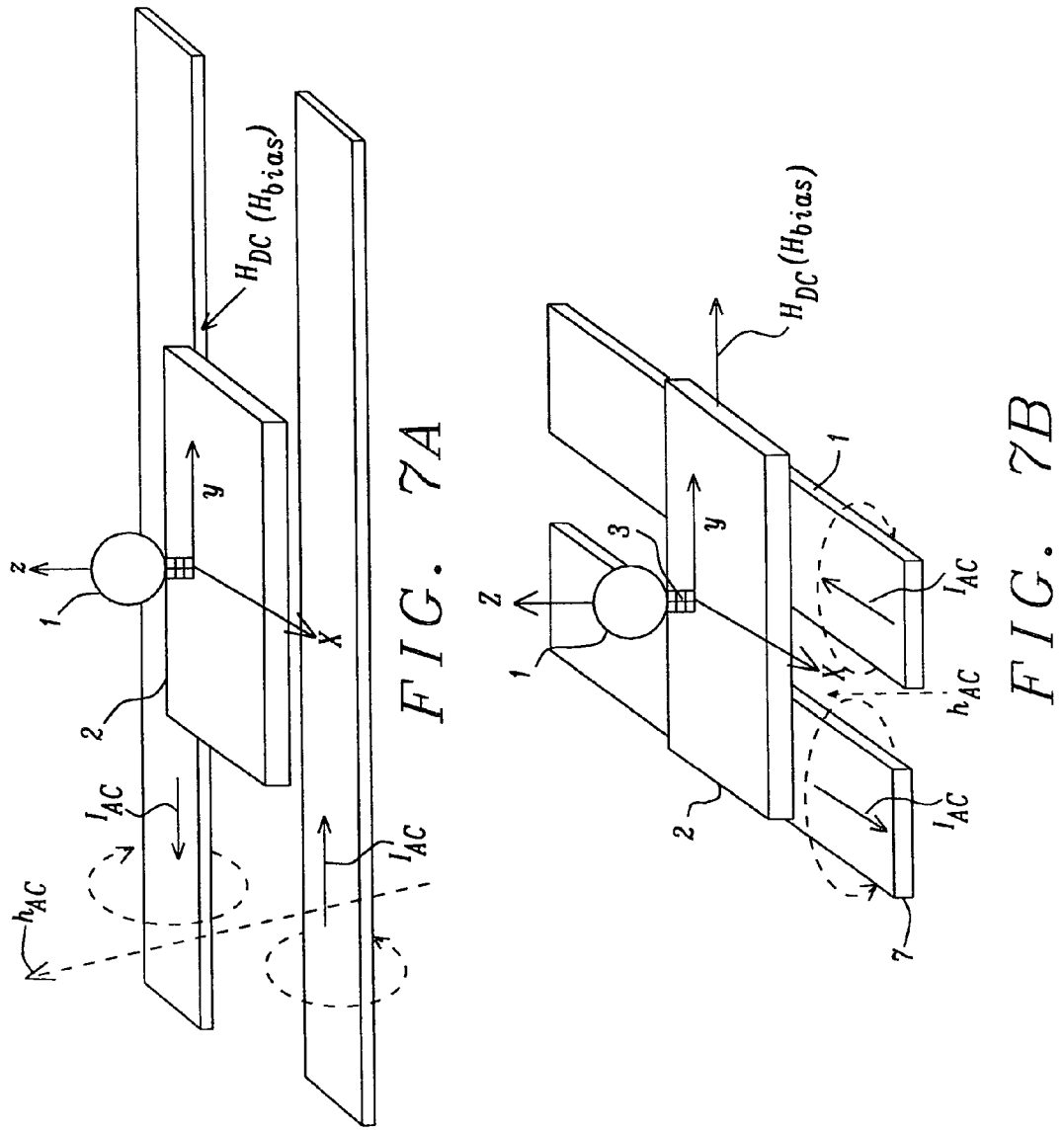

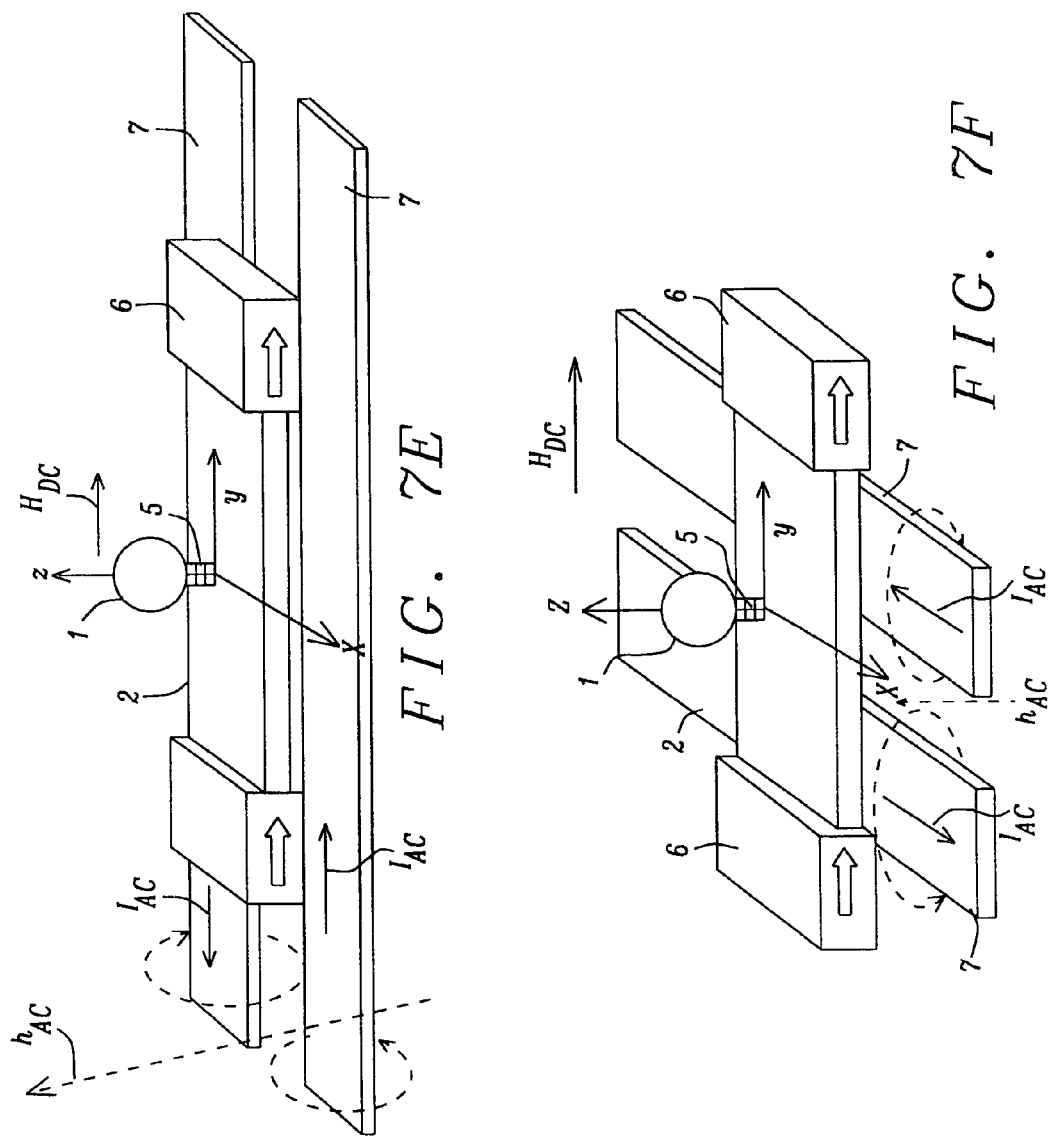

DETECTION OF MAGNETIC BEADS USING A MAGNETORESISTIVE DEVICE TOGETHER WITH FERROMAGNETIC RESONANCE

This is a divisional application of U.S. patent application Ser. No. 11/528,878, filed on Sep. 28, 2006 now U.S. Pat. No. 7,729,093, which is herein incorporated by reference in its entirety, and assigned to a common assignee.

FIELD OF THE INVENTION

The invention relates to the general field of magnetic field measurement with particular reference to that of magnetic beads that have been selectively bound to biological structures and/or large molecules.

BACKGROUND OF THE INVENTION

The invention discloses a methodology for detecting magnetic beads, magnetic particles and magnetic nano-particles by inducing ferromagnetic resonance (FMR) of their magnetic moment and by using a magneto-resistive (MR) sensor to detect the magnetic field produced by the FMR. Binding these magnetic beads or particles to biological or chemical molecules thus enables the presence of these molecules to be detected. In the form of a binding assay, where a matrix of MR sensors are patterned, this method can be used to identify the presence of a molecule of interest as well as to quantify its population. This method can address many other issues in the prior art that also utilize magnetic bead labeling and MR sensing, thus making this technology widely applicable.

Detection of biological or chemical molecules by using super-paramagnetic beads and particles as the labeling component and by using magneto-resistive sensors for detection of such labels is regarded as a promising technique to achieve accurate molecule counting with a resolution of several molecules or even a single molecule. It has the potential to enable fast, efficient, and economical biological applications, such as in-field virus and bacteria detection.

Binding assays to detect target molecules is a widely used technique in the biological, biochemical, and medical communities. The selective bindings commonly used include polynucleic acid bindings or hybridizations involving RNA and DNA, many types of ligand-to-receptor bindings, as well as antibody to antigen bindings. The target molecules in these bindings, for example, proteins or DNA, can also be a distinctive component or product of viruses, bacteria and cells, which may be the actual objects of interest for the detection.

In a binding assay, the binding molecules are attached to a solid substrate as "capture molecules". When the assay is exposed to a liquid-form sample, where the target molecules attached to a physical label are contained, the binding molecules capture the target molecules with the selective bindings and immobilize the target molecules on the surface. This capture process is called "recognition". The recognition events can be made to generate detectable signals from the attached labels and, consequently, the presence or absence of a target molecule can be detected.

In various prior art techniques utilizing the labeled binding process, the labels originally attached to the target molecule are also immobilized on the surface after the recognition process. The labels are either bound together with the target molecules on the surface ("sandwich" assay) or are by themselves ("competitive" assay). After the removal of non-bound labels, the bound labels can then be made to generate measurable signals.

When using magnetic beads or particles as the labeling component and a MR sensor as the detector, the MR devices are embedded below the binding surface and are usually covered by a protective layer. When the magnetic beads or particles are bound to the surface above a MR sensor, they can generate a magnetic field spontaneously or, in the case of super-paramagnetic beads or particles, if an applied magnetic field is present. This magnetic field from the beads or particles can be sensed by the MR device, which can then provide a voltage signal.

The magnetic labels described in published studies or as patents are usually super-paramagnetic beads—nano-particles (or larger beads that comprise nano-particles suspended in a non-magnertic matrix) that have no magnetization at room temperature without an externally applied magnetic field because of the super-paramagnetic effect. Such labels are desired in biological applications because they do not aggregate (at zero field). The beads or particles described in the prior art usually range in size from tens of nanometers to several microns. When the labels are attached to a surface after the recognition process, either single or multiple labels are attached to each MR device. However, the sensing mechanism has generally been the same for all the previous designs. When the magnetic labels are attached to the MR sensor top surface, the field generated by the magnetic moment of the beads or particles will either act directly on the underlying MR sensor or it may cancel a portion of the applied magnetic field acting on the sensor. For sensors that have no attached labels, the magnetic field from the magnetic labels is not present.

FIG. 1 is a schematic representation of the scheme outlined above. Magnetic bead 1 (which term will, hereinafter, be assumed to include magnetic beads, as well as particles and nano-particles) is attached to the MR sensor surface by the binding pairs 5 after recognition. The MR sensor used or referred is usually a giant-magneto-resistive (GMR) or a tunneling-magneto-resistive (TMR) sensor, which contains a magnetic free layer 2, a non-magnetic spacer layer 3 and a magnetic reference layer 4. Spacer 3 is usually a conductive layer for GMR sensors and insulator for TMR sensors. Magnetization of reference layer 4, as represented by $M_{reference}$ is fixed (i.e. 'pinned') in the X axis direction by an exchange field from other magnetic layers below it, which are not shown in the figure.

The pinned layer does not change its magnetization direction under normal magnetic fields. In a conventional MR sensor, a bias DC field $H_{bias}$ is usually applied in the Y direction by a pair of opposing hard magnets on the sides of the sensor, so that the free layer's magnetization will be in the Y axis direction when no magnetic field is applied. However, this free layer alignment to Y axis can also be achieved by making the sensor dimension in the Y axis longer than in X axis due to the shape anisotropy. Because of the shape anisotropy, the magnetization of the free layer 2, as represented by $M_{free}$, can only rotate freely in the XY plane when a transverse field is applied along the X axis direction and it is very difficult to rotate outside the XY plane, i.e. towards the Z axis.

If a magnetic field is applied in the X axis direction, the free layer magnetization rotates away from the Y axis and the resistance of the entire MR junction will change according to $$R = R_0 - \Delta R \cos \theta$$

where $R_0$ is the base resistance of the sensor, $\Delta R$ is the full range resistance change of the sensor and $\theta$ is the angle between the magnetization of the reference layer and the free layer. With a DC current applied to the device, where the current can either flow in the XY plane or perpendicularly through the device, the voltage across the device will change, because of the resistance change, to produce a measurable voltage signal.

In prior studies and patents, several detection schemes were used. One commonly used scheme is to apply a magnetic field in the transverse direction [4-10, 12-13], e.g. along the X axis as in FIG. 1. Super-paramagnetic beads are also used. When a super-paramagnetic bead is bound to the top surface of the MR sensor, this applied field can magnetize the bead magnetization along the field direction. The bead magnetic moment in turn will produce a magnetic field in the MR sensor below and partially cancel the original applied magnetic field acting on the MR sensor. Therefore, the voltage across the sensor when a bead is present is different than when there is no bead attached at the same applied field condition and the presence of the bead is detected by this voltage amplitude difference.

It is important to note that these prior art methods use applied magnetic fields oscillating at frequencies less than 100 kHz (often much less) whereas the present invention requires frequencies in the MHZ (and higher) region.

A reference sensor to which beads will not attach to at any time is normally used for comparison of this voltage difference. During the detection, the applied field can also be a modulated by an AC field that will induce a same frequency AC voltage across the sensor. By utilizing a lock-in technique, the signal to noise ratio can be enhanced.

Another bead sensing scheme, also known as BARC [1-3, 11], is to apply a DC field perpendicular to the film plane, i.e. along the Z axis direction in FIG. 1, with no bias field at all being present. This DC field serves to magnetize the super-paramagnetic bead moment vertically. The in plane component of the field generated by the vertical bead moment will rotate the free layer magnetizations in the upper XY plane and low XY plane towards or away from the Y axis at the same time. If the reference layer magnetization is aligned along the Y axis, or a multi-layer MR structure is used, this rotation will produce a resistance change. It is also called "scissoring mode" [11]. This scheme also needs a reference sensor for detection.

A potential problem common to all the previously published or patented bead-MR sensor detection methods is that they are prone to fluctuations in the magnetic signal. Since all these detection methods are mainly practiced in the low frequency region from several Hertz to several kHertz, 1/f noise is very significant. Although the lock-in technique can successfully suppress the noise from the electrical sources by its narrow bandwidth, the noise from magnetic sources, for example Barkhausen noise, popcorn noise and telegraph noise cannot be prevented from affecting the locked-in signal. These magnetic noise sources are related to domain and local magnetization switching of MR sensors and are always most predominant in the low frequency region and usually show up as signal level random fluctuations. For the scheme that requires a reference sensor for detection, this combined noise effect from both the detection sensor and the reference sensor will at least double this parasitic fluctuation of the signal level.

Besides the fluctuations from the sensor, the bead itself will always have shape, size and magnetic content variations as well as binding site variations. These variations will also cause fluctuations of the amount of the bead magnetic field going into the sensor. With all the noise sources added together, these can be quite large and can cause significant signal fluctuations to inhibit practical binding assay applications that are based on the detection of the absolute field strength.

Another problem specifically for the field cancellation method is that a magnetic field needs to be applied in the sensing direction, i.e. X axis, to magnetize the magnetic beads and thus generate the cancellation field. However, this relatively large amplitude field will rotate the MR sensor free layer magnetization to the place where its sensitivity is not the highest. In other words, when the bead field is highest, the sensor sensitivity is lowest. By proper design of the MR sensor film structure and by using a vertical AC field to mimic the scissoring mode, second harmonic detection [7] can minimize the sensitivity loss. But the signal generated by the cancellation effect from the bead field is significantly decreased because it is only operating with a single bead field polarity and not a full reversal of the bead field direction in the transverse direction.

For the scissoring mode, where the bead is magnetized vertically, there is no sensitivity concern. However, this mode requires a relatively large sensor size. For a sub-micron or deep submicron size sensor, the exchange energy within the free layer will degrade the amount of rotation achievable for the two regions of the sensor rotating against each other. A low bias field, $H_{bias}$, or no bias field may be needed, which can easily lead to instability in a micron size sensor because of weak or no free layer domain control. In addition, for a GMR or TMR sensor with a single free layer, since this scheme only utilizes the sensor free layer magnetization rotation between 0 and 90 degrees, half of the sensor sensitivity region is not used.

For a multilayer GMR sensor, the rotation of magnetization can theoretically reach maximum or 0 to 180 degrees. A current-in-plane (CIP) multilayer GMR sensor usually has a lower dR/R, i.e. lower signal, than the state-of-the-art TMR or carefully designed spin valve GMR sensors. The current-perpendicular-to-plane (CPP) multilayer GMR sensors although possessing a much higher dR/R than the CIP ones, have also shown extraordinary magnetically related 1/f type noise in previous studies.

This noise can be more than 10 dB over the sensor's Johnson noise level in a micron size multilayer device and it will severely degrade the SNR of the sensor. To overcome the above problems, what is needed is, first, a scheme that can avoid having the bead magnetizing field affect the sensor free layer as well as utilizing the full reversal of the bead magnetization to gain maximum signal. Second, to avoid fluctuation of the bead magnetic field or the sensor resistance due to various magnetic sources, the method should not rely on detection of the absolute bead field magnitude. Third, signal detection at much higher frequencies than currently being explored (<100 kHz), for example beyond 1 MHz, is preferred in order to reduce low frequency noise effects.

A routine search of the prior art was performed with the following references of interest being found:

[1] D. R. Baselt et al., "A biosensor based on magnetoresistance technology," *Biosens. Bioelectron.*, vol. 13, pp. 731-739, October 1998.

[2] R. L. Edelstein et al., "The BARC biosensor applied to the detection of biological warfare agents," *Biosens. Bioelectron.*, vol. 14, pp. 805-813, January 2000.

[3] M. M. Miller et al., "A DNA array sensor utilizing magnetic microbeads and magnetoelectronic detection," *J. Magn. Magn. Mater.*, vol. 225, pp. 138-144, April 2001.

[4] D. L. Graham, H. Ferreira, J. Bernardo, P. P. Freitas, and J. M. S. Cabral, "Single magnetic microsphere placement and detection on-chip using current line designs with integrated spin valve sensors: Biotechnological applications," *J. Appl. Phys.*, vol. 91, pp. 7786-7788, May 2002.

[5] H. Ferreira, D. L. Graham, P. P. Freitas, and J. M. S. Cabral, "Biodetection using magnetically labeled biomolecules and arrays," *J. Appl. Phys.*, vol. 93, pp. 7281, May 2003.

[6] G. Li et al., "Detection of single micron-sized magnetic bead and magnetic nanoparticles using spin valve sensors for biological applications," *J. Appl. Phys.*, vol. 93, pp. 7557-7559, May 2003.

[7] G. Li, S. X. Wang and S. Sun, "Model and experiment of detecting multiple magnetic nanoparticles as biomolecular labels by spin valve sesnors," *IEEE Trans. Magn.*, vol. 40, pp. 3000, 2004

[8] S. X. Wang et al., "Towards a magnetic microarray for sensitive diagnostics," *J. Magn. Magn. Mater.*, vol. 293, pp. 731-736, 2005.

[9] W. Shen, X. Liu, D. Mazumdar and G. Xiao, "In situ detection of single micron-sized magnetic beads using magnetic," Appl. Phys. *Lett.*, vol. 86, pp. 253901, 2005.

[10] H. Ferreira, N. Feliciano, D. L. Graham and P. P. Freitas, "Effect of spin-valve sensor magnetostatic fields on nano-bead detection," J. Appl. Phys., vol. 97, pp. 10Q904, 2005.

[11] D. R. Baselt, "Biosensor using magnetically detected label," U.S. Pat. No. 5,981,297 (1999) teaches that a change in output of MR sensors indicates the presence of magnetic particles.

[12] M. C. Tondra, "Magnetizable Bead Detector," U.S. Pat. No. 6,743,639 B1 (2004)

[13] M. C. Tondra, "Magnetizable Bead Detector," U.S. Pat. No. 6,875,621 B2 (2005); this, and ref. 12 above, shows an MR sensor in a bridge circuit which may comprise interconnected individual sensors adjacent to the binding molecule layer.

[14] U.S. Pat. No. 6,518,747 (Sager et al) discloses applying an AC signal to excite Hall sensors in a DC field to detect magnetic particles.

[15] U.S. Patent Application 2006/0020371 (Ham et al) discusses FMR detection of magnetic beads.

SUMMARY OF THE INVENTION

It has been an object of at least one embodiment of the present invention to provide a sensor for the detection of magnetic beads together with a method for utilizing said sensor.

Another object of at least one embodiment of the present invention has been that said sensor be relatively insensitive to the precise location of a bead relative to the sensor as well as to the exact size of the bead.

Still another object of at least one embodiment of the present invention has been that said sensor be relatively insensitive to the presence of other nearby beads.

A further object of at least one embodiment of the present invention has been that said method not require the measurement of the absolute value of a magnetic field generated by the bead.

These objects have been achieved by exciting FMR (ferromagnetic resonance) in the bead and then detecting the rotating magnetic field that the bead emits while in the resonance state. Our preferred means for detecting said rotating field has been a magneto-resistive detector such as a GMR (giant magnetic resistance) or TMJ (tunneling magnetic junction) device, though the method can be effectively used with any device capable of detecting magnetic fields as low as 1 Oe that are oscillating at frequencies in the MHz to GHz range. As a practical matter, the lowest field that can be used will be determined by the intrinsic noise discrimination and detection sensitivity of the sensor. Additionally, the detection sensitivity can usually be improved by narrowing the band width of the signal that is being detected.

The oscillating magnetic field used to excite the bead to FMR may be generated in a number of ways including external means and in-situ generation.

BRIEF DESCRIPTION OF THE DRAWINGS

FIG. 1 shows a prior art magnetic bead detector.

FIG. 2 illustrates the basic method of the invention, including the various magnetic fields that are needed to bring about FMR.

FIGS. 6A-6F show five embodiments of the invention that have the following features in common: $H_{DC}$ in the Z direction and $h_{AC}$ in the X direction.

FIGS. 7A-7D show four embodiments of the invention that have the following features in common: $H_{DC}$ in the Y direction and $h_{AC}$ in the Z direction.

FIGS. 7E-7F show two embodiments similar to FIGS. 7A and 7B respectively, but with $H_{bias}$ provided by external magnets as in FIG. 5A.

DESCRIPTION OF THE PREFERRED EMBODIMENTS

In the detection schemes to be described below, a uniform magnetization of the magnetic bead is assumed. The bead is only required to have a magnetic moment, either spontaneous or induced, when in the field. FIG. 2A shows a schematic view of the detection of FMR in an excited magnetic bead by a MR sensor. Free layer 2 of the MR sensor is in the XY plane. A Y axis direction DC field $H_{bias}$ (applied or anisotropy driven) in the sensor serves to maintain the free layer magnetization along the Y axis direction when there is no transverse X axis field applied. Note that, although we refer to a free layer when we describe the invention, we do so as a matter of convenience rather than to exclude other methods for detecting magnetic fields such as normal (i.e. not giant) magnetoresistance.

Magnetic bead 1 lies above the top surface of the sensor. An externally applied static field $H_{DC}$ perpendicular to the sensor film plane orients the bead magnetization in the Z axis direction. Since the sensor only responds to X axis direction transverse fields, this DC field will not cause sensor resistance to change. Then, a low amplitude, high frequency, sinusoidal AC field $h_{AC}$ is applied in the Y axis direction to induce ferromagnetic resonance of the bead magnetization. This Y axis sinusoidal field does not itself cause the free layer magnetization to rotate as long as it is much smaller than $H_{bias}$.

Basis of the Invention:

In FIG. 2 we illustrate the basic effect of FMR on the magnetic moment of a bead excited by an AC magnetic field $h_{AC}$ in the presence of a DC magnetic field $H_{DC}$. MR sensor magnetization is oriented in the Y axis direction by a bias DC field $H_{bias}$. The magnetic field generated by the resonating bead's magnetic moment is sensed by the MR sensor's free layer below. The X component of the resonating bead's moment generates a transverse field in the sensor free layer which leads to an AC voltage across the sensor at the FMR frequency.

Figure 3:
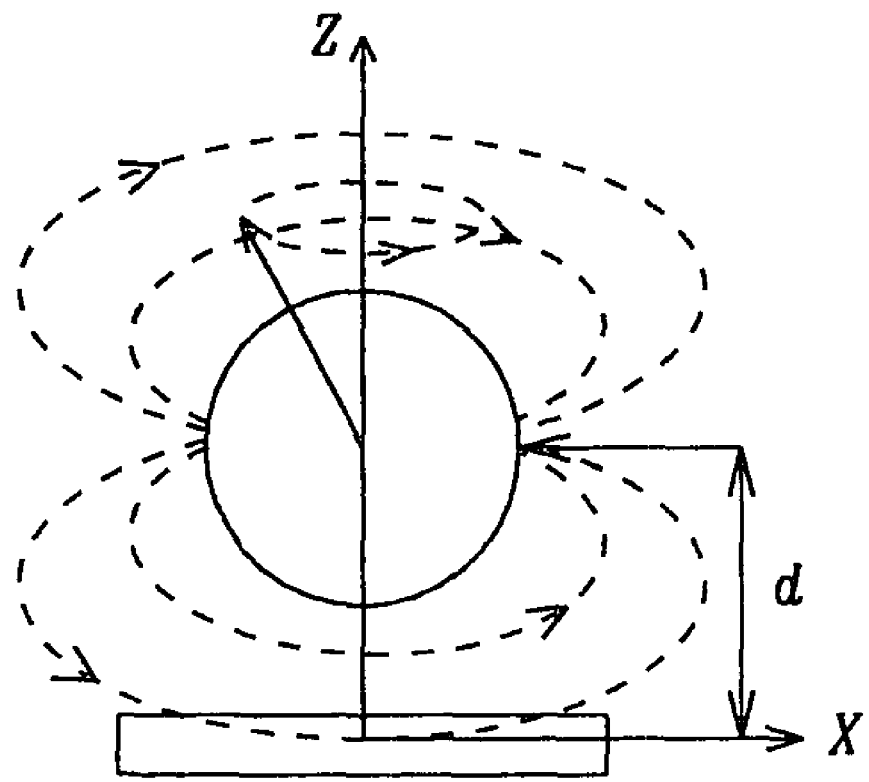
FIG. 3 is FIG. 2 viewed along the Y direction.

As shown in FIG. 3, this causes the free layer magnetization to rotate. Since $m_x$ has the same frequency, the free layer magnetization will be modulated at this frequency by the bead field. This modulation further leads to a voltage alternating at the same frequency as that of the sensor (which usually implies the free layer). Thus, by tuning the structure so as to achieve resonance, one can be certain that any modulation of the sensor's output derives from the bead(s).

Figure 4:
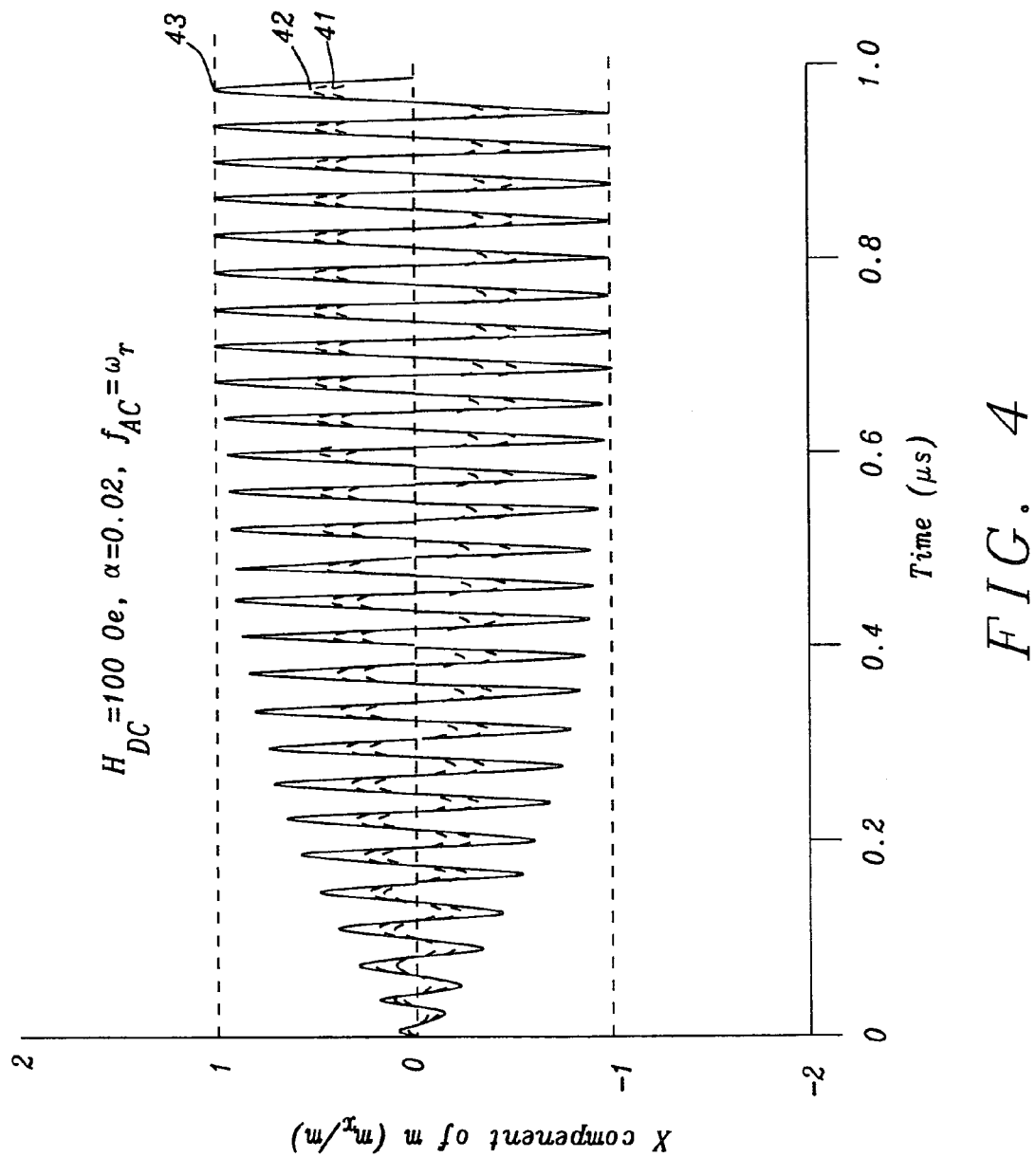
FIG. 4 plots the X component of the bead magnetization vs. time after the AC field is applied in the Y axis direction for three different values of $h_{AC}$.

FIG. 4 shows simulation of the X component of the magnetic bead's moment as a function of time for the detection structure shown in FIG. 2. $H_{DC}$ for the simulation was 100 Oe, a damping constant of about 0.02 was used, with the Y axis AC field ($h_{AC}$) frequency being that of the bead resonance frequency $\omega_r$, for a 100 Oe field (279.73 MHz). Results for three different values of $h_{AC}$ are shown. Curve 41 is for 1 Oe, curve 42 is for 2 Oe, and curve 43 is for 5 Oe. These show that, for a 0.02 damping constant, a 5 Oe AC field is already enough to generate a full amplitude resonance of the bead moment, i.e. $m_x = m_{bead}$, at the given condition.

In first order calculations, the super-paramagnetic effect is not considered. For super-paramagnetic beads, a $h_{AC}$ field beyond 10 Oe may not be trivial for an $H_{DC}$=50 Oe or 100 Oe. The AC field can also cause the bead moment to vary in magnitude instead of just direction.

Besides the comparison of the oscillation amplitude of bead moment at different frequencies or different DC fields, another way to detect the presence of a magnetic bead is to check the existence of an $m_x$ component at an AC field near or at a bead's resonant frequency at the given DC field. When there is no bead, no $m_x$ component is present. This method is an absolute signal level detection method so it is susceptible to bead field strength variations from various sources as in the prior art. However, it still has the advantage of detection at the bead FMR that produces the largest $m_x$ amplitude, i.e. highest detectable signal, using a relatively small excitation AC field.

The $m_x$ component of the bead magnetic moment will linearly influence the sensor's resistance change. Several previous studies [7, 10] demonstrated a straightforward way to estimate the signal level from a GMR or TMR sensor with a given magnetic bead that has a magnetic moment in the X axis direction. The MR signal from the bead moment was reported to usually be a small portion of the entire dynamic range of the MR sensors, i.e. less than 1% to several percent of the dR/R. The signal of the bead FMR at the resonance frequency should be high enough to be picked up by available RF electronics with an applicable signal-to-noise-ratio (SNR). For example, in thermally excited FMR in GMR sensors, usually in the several GHz region and corresponding to less than 0.1% resistance fluctuation, has already been successfully measured with relatively simple RF circuitry [25]. Therefore, FMR detection schemes proposed for monitoring the $m_x$ component of the bead magnetic moment should be achievable by measuring the MR sensor voltage output.

In summary, use of FMR to detect the presence of beads offers the following advantages:

1. The MR sensor responds to only the bead field during detection. The DC field for magnetizing super-paramagnetic beads and the AC excitation field can be applied in other than the sensing direction of the MR sensor. Thus there is no tradeoff needed between sensitivity and bead magnetic signal. In addition, it allows for adjustment of the sensor bias field towards lower values to enhance the sensor sensitivity to transverse fields.

2. For a bead of low damping material, only a relatively small AC field is needed to excite full amplitude resonance in the bead so as to produce the maximum AC field in the sensing direction of the MR sensor.

3. The method is minimally affected by low frequency parasitic magnetic fluctuations. The excited FMR of the bead magnetic moment, under moderate magnetic fields. is usually at a frequency beyond the Barkhausen noise, popcorn noise, telegraph noise, and 1/f noise active regions. For example, the FMR frequency at a DC field of 100 Oe is about 280 MHz.

4. A reference sensor is not needed for signal detection. Measurement of the relative amplitude or phase of the FMR signal at different AC field frequencies at a constant DC field, or at the same AC field frequency but varying DC fields, will indicate the presence of a magnetic bead. For example, by keeping the DC and AC field amplitudes constant while sweeping the AC field frequency from a value lower than $\omega_r$ to a frequency higher than $\omega_r$, while simultaneously measuring the sensor signal at the same frequency. When a magnetic bead is present the sensor signal peaks at $\omega_r$ but if there is no bead, the signal vs. AC field frequency will stay flat. Peak detection of the swept curve can thus be used as an indicator of a bead's presence.

5. The method is insensitive to the precise location of the binding site of the bead on the MR sensor. In absolute field level detection methods the magnetic field level that the sensor sees (due to the bead) will be different for different binding sites. However, as discussed in the preceding paragraph, the frequency dependence of the signal on the AC field frequency will stay the same for a given bead. Therefore, if detection is achieved by sweeping the AC field frequency, local binding site variations will not affect the peaking of the AC signal at $\omega_r$.

6. The method is relatively insensitive to bead size distribution. Field cancellation methods are strongly affected by the beads' physical size distribution because each bead's magnetic moment is proportional to its volume. With a large bead size distribution, the magnetic field from the beads will fluctuate substantially. For FMR detection, however, although bead size variations will still cause the absolute signal level to fluctuate, as long as the beads' composition and shape are the same, the frequency dependence of the AC signal from each bead still stays the same. As long as this frequency dependence is used for detecting the beads' presence (and assuming sufficient bead field strength) the scheme that is taught by this invention will be insensitive to the bead size distribution.

7. The method is insensitive to the bead-sensor distance (see d in FIG. 3). Longer biological or chemical binding pair lengths will lead to longer distances between bead and sensor, which will decrease the absolute level of the bead magnetic field at the sensor. However, for the FMR detection scheme, as long as the bead-sensor distance is within a range that is low enough to show a dependence of the FMR signal on the AC field frequency, this physical distance variation can be tolerated. This insensitivity results in having greater flexibility when choosing biological and chemical binding pairs.

8. The method enables field effects from neighboring beads to be minimized. The AC field needed to evoke full amplitude FMR in a bead with a relatively small damping constant is usually small (several Gauss). An AC field of this magnitude can be generated by passing an AC current through a conductive stripe that runs beneath a row or column of sensors or even by an individual line underneath each sensor, which excites only the beads directly above the stripe lines. Neighboring beads not over the stripe line will not contribute to the signal generated by the sensor.

This feature may be used as the basis for a method to determine the spatial location of a single bead which may, or may not, be part of an array of similar, or identical, beads. Se feature (g) below.

9. Since the resonance frequency is a function of the shape anisotropy of the magnetic beads and their damping constants, the method facilitates the simultaneous use of multiple beads whose resonance frequencies are not necessarily all the same, even in the same DC field. Examples include, but are not limited to, elongated magnetic beads and beads with a magnetic shell and a non-magnetic core. These structures will have different FMR frequencies from a spherical magnetic bead because of the shape anisotropy. It is also possible to vary the damping constant of the bead through control of its composition in order to shift the FMR frequency. In addition, magnetic beads formed from magnetic particles suspended in a nonmagnetic matrix will also exhibit different FMR resonance behavior, depending on the densities of the particles in the matrix.

10. The method offers a way to quantify the number of beads attached to a given sensor from the resonance frequency shift caused by the magneto-static interaction between beads attached to the same sensor. From the FMR frequency shift of the ensemble of the beads, the number and formation of the beads on the sensor surface is obtainable after careful characterization and calculation.

Features of the Method

All necessary layers, coatings and structures that enable the MR sensor to function in the relevant biological or chemical environments are assumed in the embodiments.

The magnetic beads used in the embodiments vary in shape, structure and composition as needed to obtain different bead FMR frequencies under the same DC field to enable bead labeling. The applied DC magnetic field in the following embodiments is also the field used to magnetize the beads should they be super-paramagnetic.

The MR sensor for FMR detection is not limited to GMR and TMR sensors, but rather any thin film sensing device that can show a measurable change in the presence of a magnetic field. The excited FMR of the bead moment produces an AC magnetic field in the MR sensor and subsequently an AC voltage signal across the sensor when a sensing current is applied. The detection of the presence of the bead can be achieved by the following methods (list not intended to be exhaustive):

(a) Sensor signal amplitude dependence on the AC field frequency when DC field is fixed. The amplitude is preferably measured at the same frequency as the AC field.

(b) Sensor signal amplitude dependence on the DC field when AC field frequency is fixed. The amplitude is preferably measured at the same frequency as the AC field.

(c) Sensor signal phase dependence on the AC field frequency when DC field is fixed. The phase should be measured at the same frequency as the AC field.

(d) Sensor signal phase dependence on the DC field when AC field frequency is fixed. The phase should be measured as close to the AC field frequency as possible.

(e) The existence of an AC signal from the sensor at the frequency of the driving AC field, preferably near or at bead's resonant frequency.

(f) Cancellation of the driving AC field on the sensor at a frequency preferably near or at bead's resonant frequency.

(g) Determining the precise location of a bead. In a conventional MRAM (magnetic random access memory), two non-parallel sets of conductive wires are used to form an array in which the intersection of any two wires (from opposing sets) is made to be unique by providing the same input to each wire, namely slightly more than half the magnetic field needed to trigger a single device. Consequently, it is only at the intersection of the two wires that the local field becomes strong enough to trigger a device.

Figure 9:
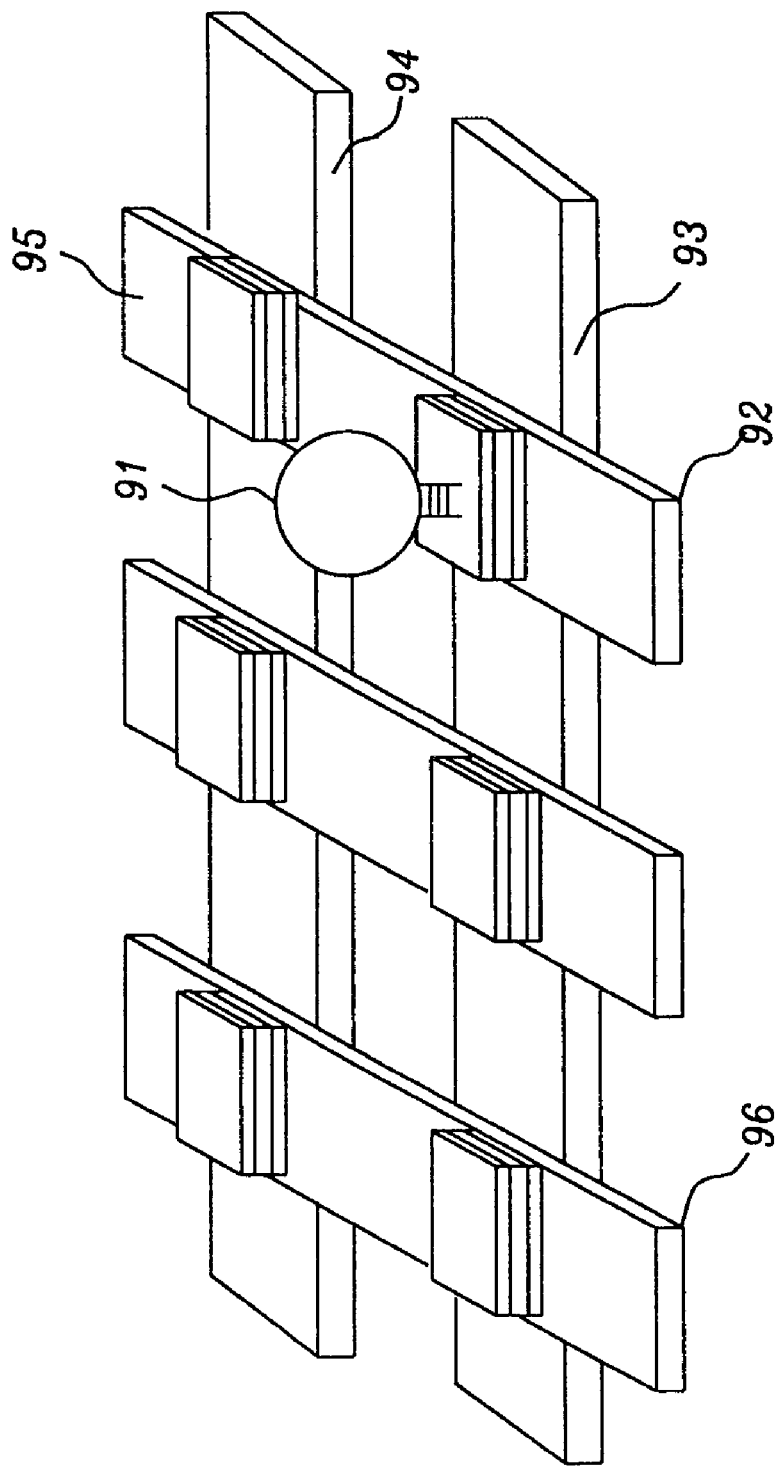
FIG. 9 illustrates a method for determining the spatial location of any particular bead that is part of an array of beads.

In the present invention, the inputs provided to the two intersecting differ from one another. Referring now to FIG. 9, $H_{DC}$ is provided by external means and $I_{AC}$ (to generate $h_{AC}$) is sent down one of the lines which we will (arbitrarily) designate as line 92. A DC current $I_{DC}$ is sent down one of the non-parallel lines which we will (arbitrarily) designate as line 93, thereby generating a static magnetic field $h_{DC}$. All beads on lines that run parallel to line 92 (e.g. line 96) are powered so that they 'see' $h_{AC}$ and $H_{DC}$ while all beads on lines that run parallel to line 93 (e.g. line 94), except at the intersection, will see only $H_{DC}+h_{DC}$. Thus, only bead 91, located at the intersection, will also see $h_{AC}$ so it will exhibit FMR, but at a different frequency from any beads lying along line 92, 96, etc.

Comments:

For methods (a) through (d), when a bead is present, the mentioned frequency or DC field dependence is observed. When there is no bead, no dependence is seen.

For method (e), the absolute value of the bead field is detected i.e. if there is no bead there is no field. This method is susceptible to bead field strength fluctuations caused by various sources. However, it still has the advantages that when detection is in the high frequency region, the MR sensor is at its maximum sensitivity and maximum bead magnetic field at a small FMR excitation field. Note that, for method (e) the AC field is not to be applied in the sensing direction of the MR sensor.

For method (f), the absolute combined total field of the applied AC field and the bead field is detected. When there is no bead, there is no bead field acting against the AC field effect on the sensor. This method is thus similar to (e) and enjoys the same advantages as (e) over the field cancellation methods of the prior art. In (f), however, the AC field is applied in the sensing direction of MR device.

For method (g), $H_{DC}$ is typically in the range of from about 1 and 1,000 Oe while $h_{DC}$ is typically in the range of from about 1 to 100 Oe. For example, for $H_n=100$ Oe and $h_n=20$ Oe, FMR for beads on line 1 will occur at about 280 MHz while for a bead at the intersection of lines 92 and 93 it will occur at about 285.6 MHz.

STRUCTURAL EMBODIMENTS OF THE INVENTION

Listed below are the preferred structural embodiments of this invention. Note that, although each of these depicts only a single bead over each sensor, it is clear that extension to multiple beads per sensor is readily implemented.

1. Embodiment 1A

Figure 5A:
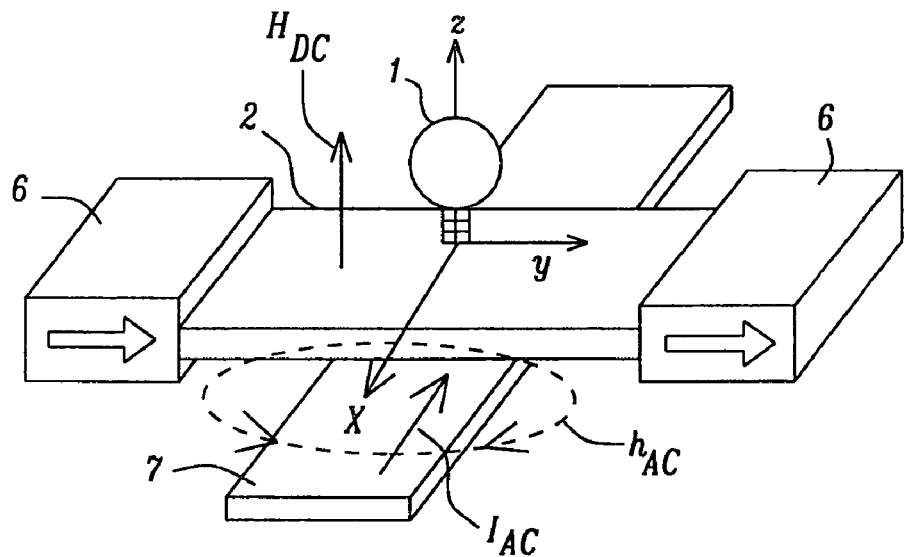
FIGS. 5A-5D show four embodiments of the invention that have the following features in common: $H_{DC}$ in the Z direction and $h_{AC}$ in the Y direction.

Referring to FIG. 5A, the magnetic bead 1 is attached to the MR sensor 2 through biological or chemical binding pair 5 following a recognition process. Two permanent magnets 6 on the sides of the sensor provide a biasing field in the MR sensor to orient the sensing layer magnetization in the Y axis direction. A static field $H_{DC}$ is applied perpendicular to the sensor plane in the Z axis direction. This static field determines the FMR frequency of the bead magnetic moment. It also magnetizes the bead when the bead is super-paramagnetic. A stripe line (or lines) 7 exists underneath the sensor or between the sensor and the bead, where an AC current $I_{AC}$ is used to produce an AC magnetic field $h_{AC}$ in the Y axis direction to excite the FMR of the bead magnetic moment. The bead FMR then produces a rotating component in the XY plane. The MR sensor 2 detects the oscillating magnetic field

2. Embodiment 1B

Figure 5B:
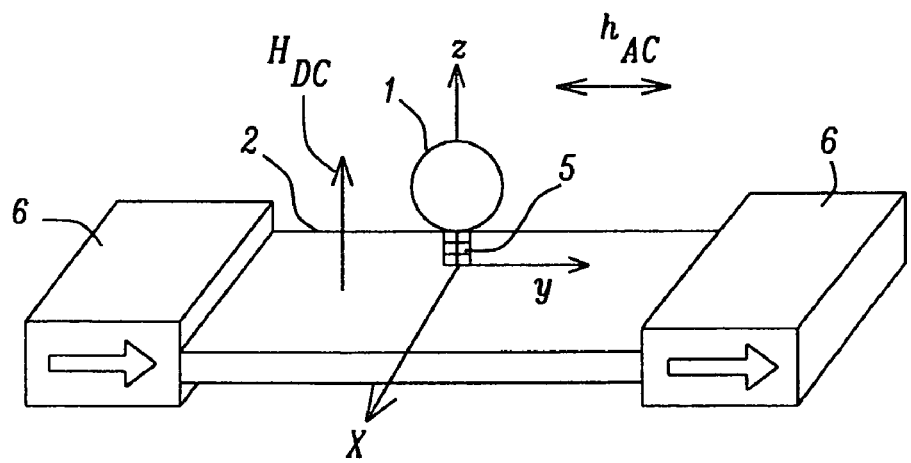

Referring to FIG. 5B, every other aspect is the same as embodiment 1A except that the AC magnetic field $h_{AC}$ in the Y axis direction is generated not by stripe line (or lines), but externally by other means. For example, RF coils or electromagnetic waves in a microwave cavity.

3. Embodiment 1C

Figure 5C:
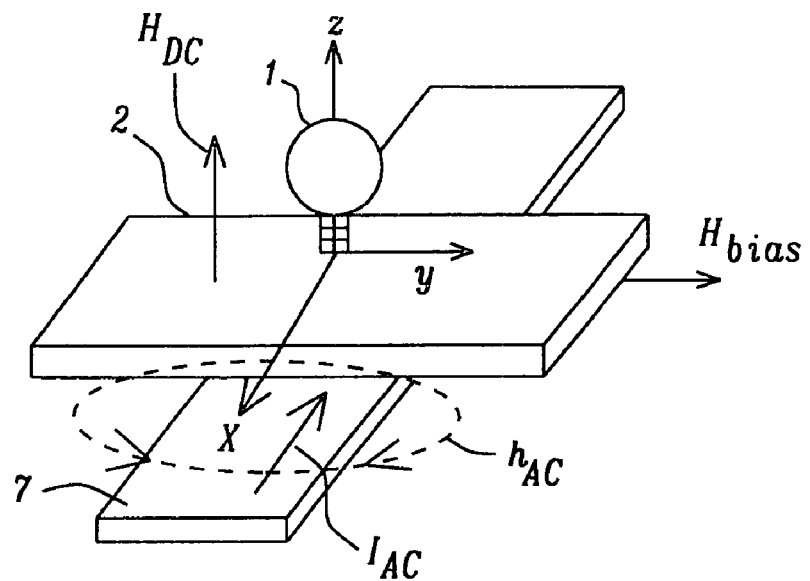

Referring to FIG. 5C, every other aspect is the same as embodiment 1A except that biasing DC field $H_{bias}$ is applied externally or generated by the anisotropy field of the sensor. $H_{DC}$ (and $H_{bias}$ as well if applied externally) determines the FMR frequency of the bead magnetic moment.

4. Embodiment 1D

Figure 5D:
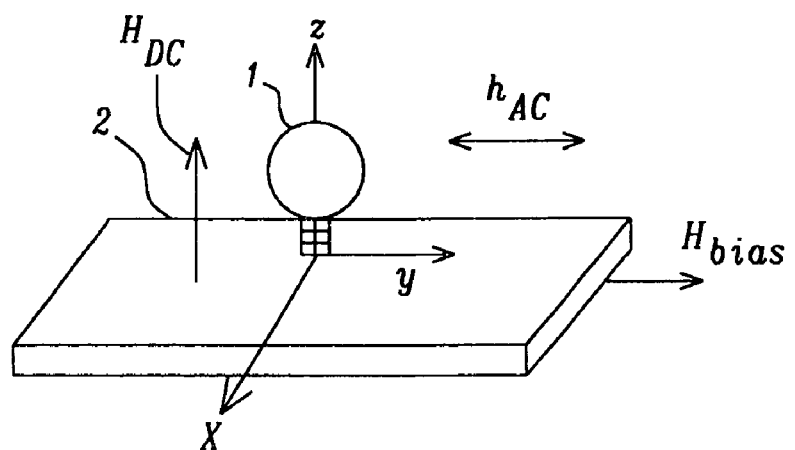

Referring to FIG. 5D, every other aspect is the same as embodiment 1C except that the AC magnetic field $h_{AC}$ is generated not by stripe line (or lines), but externally by other means. For example, RF coils or electromagnetic waves.

5. Embodiment 2A

Figures 6A, 6B:
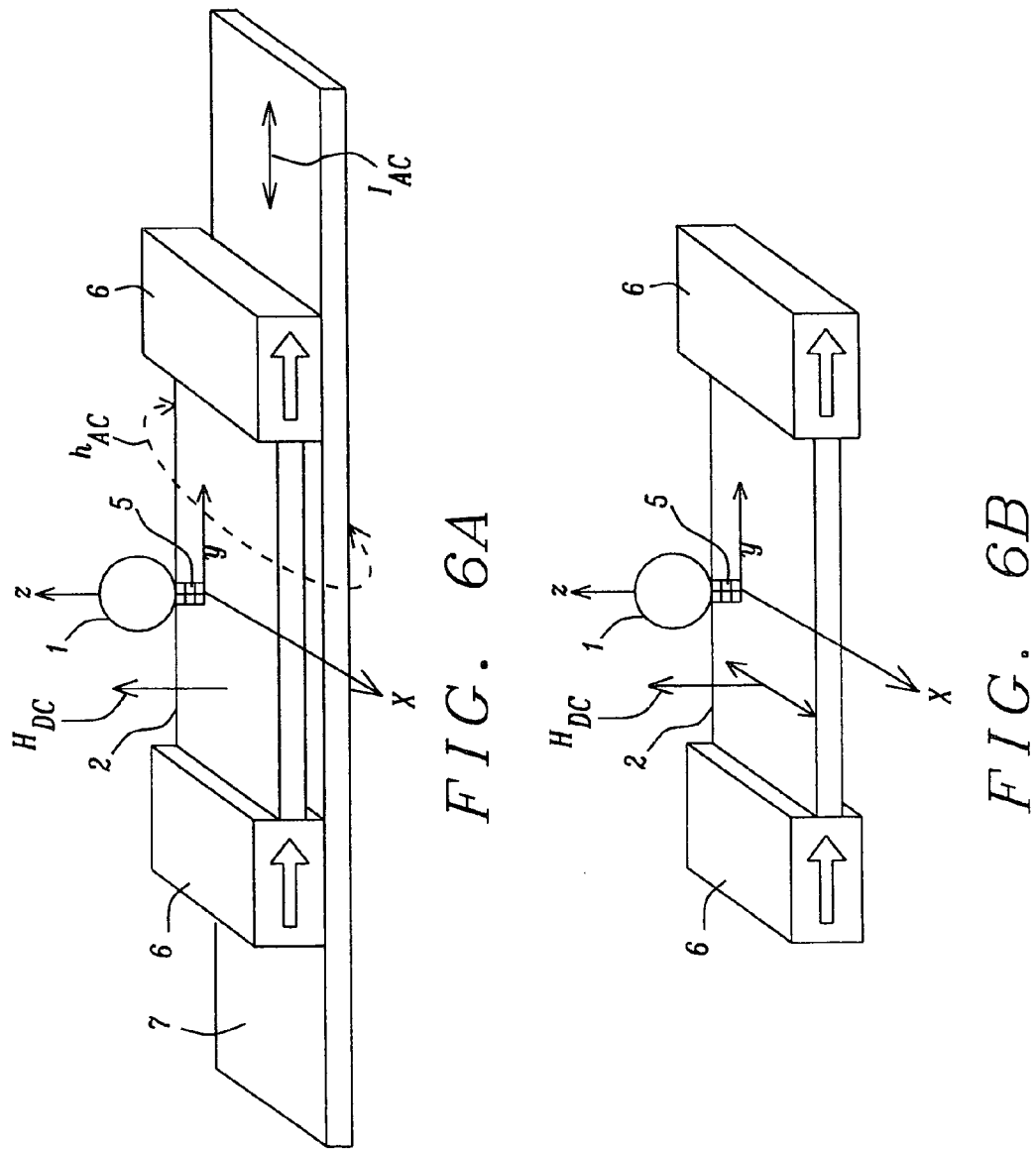

Referring to FIG. 6A, every other aspect is the same as embodiment 1A except that the stripe line (or lines) 7 that is underneath the sensor or between the sensor and the bead, is now used to produce an AC magnetic field $h_{AC}$ in the X direction to excite the FMR of the bead magnetic moment when an AC current $I_{AC}$ flows through it. The MR sensor 2 detects both $h_{AC}$ and the field generated by the bead moment. The difference of the bead field cancellation of $h_{AC}$ in the MR sensor at different driving frequencies can be used as the mechanism for detection. The cancellation of $h_{AC}$ is preferably measured in the same phase as $h_{AC}$. Since $m_X$ has the maximum amplitude and is the exact same phase as $h_{AC}$ when the frequency of $h_{AC}$ is the same as the FMR frequency of the magnetic bead in the DC field $H_{DC}$, the dependence of the cancellation effect on the AC field frequency will be more pronounced when measured at the same phase as $h_{AC}$

6. Embodiment 2B

Referring to FIG. 6B, every other aspect is the same as embodiment 2A except that the AC magnetic field $h_{AC}$ in the X axis direction to excite the FMR of the bead magnetic moment is generated not by a stripe line (or lines), but externally with other means. For example, RF coils or electromagnetic waves.

7. Embodiment 2C

Referring to FIG. 6C, every other aspect is the same as embodiment 2A except that the biasing DC field $H_{bias}$ is applied externally or generated by the anisotropy field of the sensor. $H_{DC}$ (and $H_{bias}$ as well if applied externally) determines the FMR frequency of the bead magnetic moment.

8. Embodiment 2D

Referring to FIG. 6D. every other aspect is the same as embodiment 2C except that the AC magnetic field $h_{AC}$ in the X axis direction to excite the FMR of the bead magnetic moment is generated not by a stripe line (or lines), but externally by other means. For example, coils or electromagnetic waves.

9. Embodiment 2E

Figure 6E:
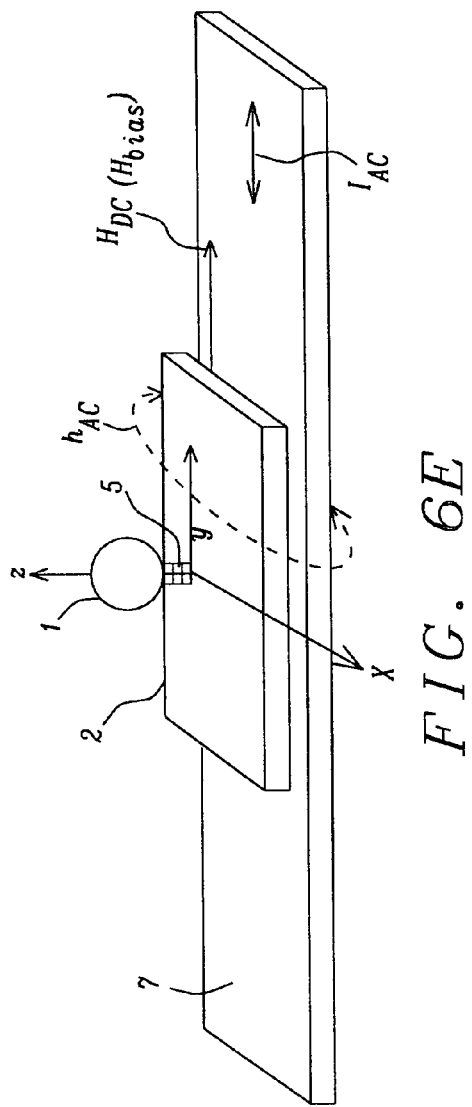

Referring to FIG. 6E. every other aspect is the same as embodiment 2A except that the DC field $H_{DC}$ is applied in the Y axis direction, which also serves as a biasing field to orient the sensor layer magnetization of the MR sensor in the Y axis direction.

10. Embodiment 2F

Figure 6F:
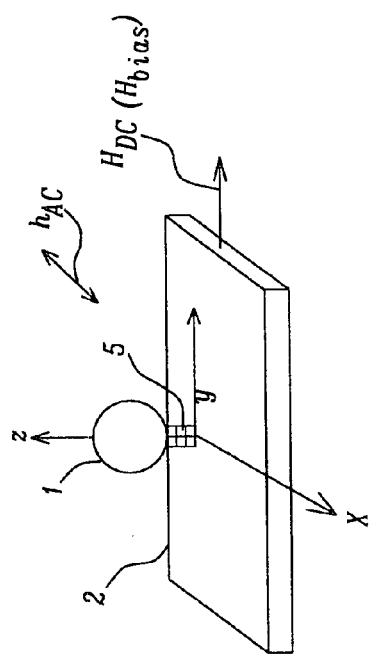

Referring to FIG. 6F every other aspect is the same as embodiment 2E except that the AC magnetic field $h_{AC}$ in the X axis direction to excite the FMR of the bead magnetic moment is generated not by a stripe line (or lines), but externally by other means. For example, RF coils or electromagnetic waves.

11. Embodiment 3A

Referring to FIG. 7A, bead 1 is attached to the MR sensor 2 through biological or chemical binding pair 5 after the recognition process. A DC field $H_{DC}$ is applied in the sensor plane in the Y axis direction. $H_{DC}$ determines the FMR frequency of the bead magnetic moment and can also serve as a bias field to orient the sensor layer magnetization of the MR sensor in the Y axis direction. It also magnetizes the bead when the bead is super-paramagnetic. An AC magnetic field $h_{ac}$ is applied in the Z direction to excite the FMR of the bead magnetic moment. This AC field is generated by a pair of stripe lines 7 on the sides or over the top or underneath the MR sensor. The AC currents flowing in the lines are constantly in the opposite direction to produce a net vertical AC field in the sensor. The MR sensor 2 detects the field generated by the bead moment during the excited FMR.

12. Embodiment 3B

Referring to FIG. 7B, every other aspect is the same as embodiment 3A except that the pair of stripe lines 7 that produce the AC magnetic field $h_{AC}$ in the Z direction is now oriented in the X direction. As a matter of fact, this pair of lines can be oriented in any direction in the XY plane as the Z axis field is not affected by their orientation.

13. Embodiment 3C

Figure 7C:
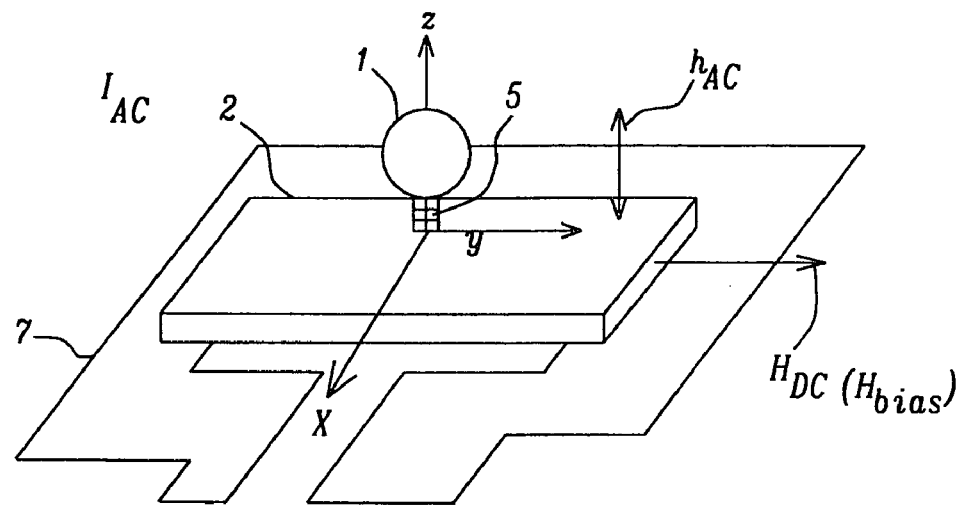

Referring to FIG. 7C, every other aspect is the same as embodiment 3A except that the AC magnetic field $h_{AC}$ in the Z axis direction to excite the FMR of the bead magnetic moment is generated by coil 7 (single or mufti turn) around, below or above the top of the sensor. The AC current flowing in the coil produces a vertical AC field.

14. Embodiment 3D

Figure 7D:
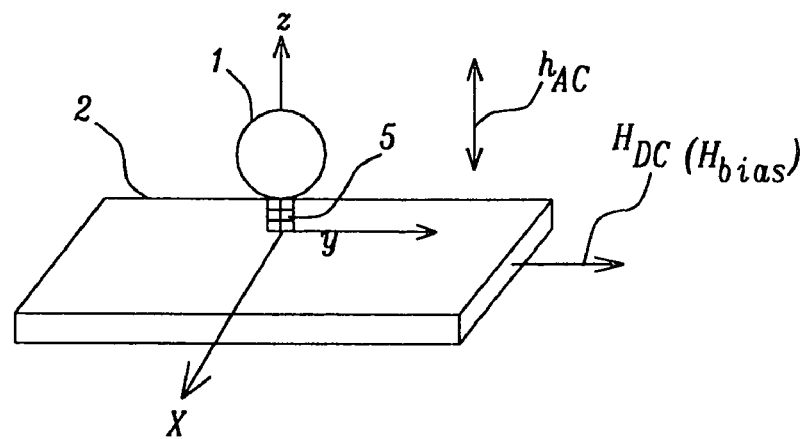

Referring to FIG. 7D, every other aspect is the same as embodiment 3A except that the AC magnetic field $h_{AC}$ in the Z direction to excite the FMR of the bead magnetic moment is applied externally with RF coils or electromagnetic waves. This leads to a voltage signal of the same frequency being generated by the sensor when there is a DC current flowing through the sensor. Because $m_x$ magnitude is a function of frequency, the voltage signal generated by the MR sensor at the same AC field amplitude but different AC field frequencies will have different output amplitudes as well. This amplitude dependence of the sensor's voltage output on frequency can be used as the mechanism for the detection of the presence of the magnetic beads. When a bead is not present, the sensor will theoretically have no output dependence on the AC field frequency because of the absence of the bead $m_x$ component.

15. Embodiments 3E and 3F

Referring to FIGS. 7E and 7F, these are the same as embodiments 3A and 3B respectively, except that the longitudinal bias is supplied by permanents as shown, for example, in FIG. 5A.

16. Embodiments 4A and 4B

Figure 8A:
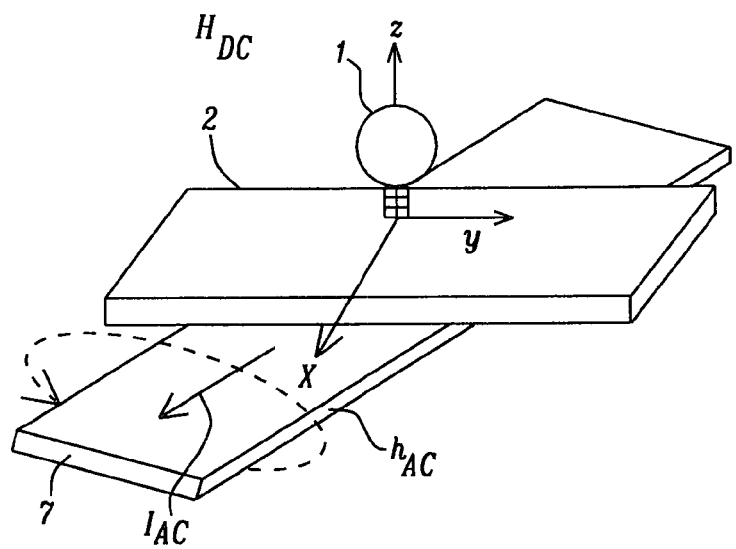
FIGS. 8A-8B are similar to FIGS. 5 thru 6 and FIG. 7, respectively, except that the overlapping field generating stripes are not required to be orthogonal to one another.
Figure 8B:
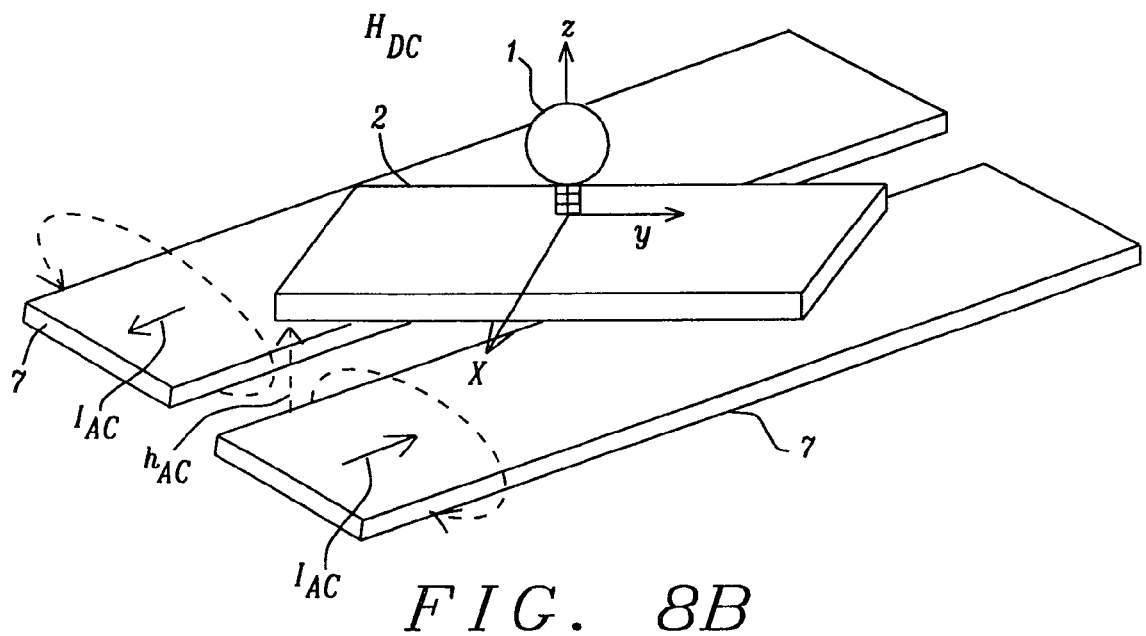

Referring to FIGS. 8A and 8B, these relate to embodiments 1A-2F and 3A, 3B, 3E, 3F respectively but show that the field generating stripes and the free layer's long axis do not have to be orthogonal to one another but, rather, are required only to be as close to coplanar as their thickness permits.

In addition, the phase of m, relative to $h_{AC}$, will also show frequency dependence. With the MR sensor free layer resistance closely following the field from the $m_x$, this phase dependence on the $h_{AC}$ frequency will also show up in the sensor's AC voltage signal and can be used as a detectable physical quantity as well.

What is claimed is:

1. A magnetic bead detector, comprising:
a free layer having a length that runs in a Y direction and a width that runs in an orthogonal X direction;
said detector being constructed to signal the presence of a magnetic field through a change in said free detector's electrical resistance;
said detector having an upper surface that is parallel to said free layer;
said free layer being magnetized in the Y direction whereby said free has a magnetic bias;
said magnetic bead being attached to said upper surface at a binding site;
an alternating magnetic field, in the Y direction, having a frequency ranging from about 1 to 10,000 MHz and an amplitude ranging from about 0.1 to 50 Oe; and
a static magnetic field, having a value of between about 1 and 10,000 Oe, in a direction normal to said upper surface.

2. The bead detector described in claim 1 wherein said free layer magnetic bias is generated by a pair of opposing permanent magnets that lie near said upper surface and wherein there is located beneath or above said detector a conductive stripe running in the X direction, thereby providing means for generating said alternating field when a current is passed through said stripe.

3. The bead detector described in claim 1 wherein said free layer magnetic bias is generated by a pair of opposing permanent magnets that lie near said upper surface and wherein there are means, external to said sensor, for providing said alternating field.

4. The bead detector described in claim 1 wherein said free layer magnetic bias is generated by a magnetic field external to said sensor or through shape anisotropy of said free layer and wherein there is located beneath or above said detector a conductive stripe running in the X direction thereby providing means for generating said alternating field when a current is passed through said stripe.

5. The bead detector described in claim 1 wherein said free layer magnetic bias is generated by a magnetic field external to said sensor or through shape anisotropy of said free layer and wherein there are means, external to said sensor, for providing said alternating field.

6. A magnetic bead detector, comprising:
a free layer having a length that runs in a Y direction and a width that runs in an X direction that is not parallel to said Y direction;
said detector being constructed to signal the presence of a magnetic field through a change in said detector's electrical resistance;
said detector having an upper surface that is parallel to said free layer;
said free layer being magnetized in the Y direction whereby said free layer has a magnetic bias;
said magnetic bead being attached to said upper surface at a binding site;
an alternating magnetic field, in the X direction, having a frequency ranging from about 1 to 10,000 MHz and an amplitude ranging from about 0.1 to 50 Oe; and
a static magnetic field, having a value of between about 1 and 10,000 Oe, and a direction.

7. The bead detector described in claim 6 wherein said X and Y directions are orthogonal and said free layer magnetic bias is generated by a pair of opposing permanent magnets that lie near said upper surface and wherein said direction of said static magnetic field is normal to said upper surface and wherein there is a conductive stripe located beneath said detector running in the Y direction, thereby providing means for generating said alternating field in the X direction when a current is passed through said stripe.

8. The bead detector described in claim 6 wherein said X and Y directions are orthogonal and said free layer magnetic bias is generated by a pair of opposing permanent magnets that lie near said upper surface and wherein said direction of said static magnetic field is normal to said upper surface and wherein there are means, external to said sensor, for providing said alternating field.

9. The bead detector described in claim 6 wherein said X and Y directions are orthogonal and said free layer magnetic bias is generated by a pair of opposing permanent magnets that lie near said upper surface and wherein said direction of said static magnetic field is normal to said upper surface and wherein there is a conductive stripe located beneath said detector running in the Y direction, thereby providing means for generating of said alternating field in the X direction when a current is passed through said stripe.

10. The bead detector described in claim 6 wherein said X and Y directions are orthogonal and said free layer magnetic bias is generated by a pair of opposing permanent magnets that lie near said upper surface and wherein said direction of said static magnetic field is normal to said upper surface and wherein there are means, external to said sensor, for providing said alternating field.

11. The bead detector described in claim 6 wherein said X and Y directions are orthogonal and said free layer magnetic bias is generated by a pair of opposing permanent magnets that lie near said upper surface and wherein said direction of said static magnetic field is normal to said upper surface and wherein there is a conductive stripe located beneath said detector running in the Y direction, thereby providing means for generating said alternating field in the X direction when a current is passed through said stripe.

12. The bead detector described in claim 6 wherein said X and Y directions are orthogonal and said free layer magnetic bias is generated by a pair of opposing permanent magnets that lie on said upper surface and wherein said direction of said static magnetic field is normal to said upper surface and wherein there are means, external to said sensor, for providing said alternating field.

13. The bead detector described in claim 6 wherein said X and Y directions are not orthogonal.

14. A magnetic bead detector, comprising:
a free layer having a length that runs in a Y direction and a width that runs in a non-parallel X direction;
a Z direction orthogonal to both X and Y directions;
said detector being constructed to signal the presence of a magnetic field through a change in said free layer's electrical resistance;
said detector having an upper surface that is parallel to said free layer;
a static magnetic field, having a value of between about 1 and 10,000 Oe, in the Y direction;
said free layer being magnetized in the Y direction by said static magnetic field, thereby giving a magnetic bias to said free layer;
said magnetic bead being attached to said upper surface at a binding site; and
a pair of conductive stripes disposed to lie on opposing sides of said detector, thereby providing means for generating an alternating magnetic field, in a frequency range that exceeds about 1 MHz, between said stripes in the Z direction when currents, running in opposing directions in opposing stripes, pass through said stripes.

15. The bead detector described in claim 14 wherein said conductive stripes run in the Y direction on opposing sides of said sensor.

16. The bead detector described in claim 15 wherein said magnetic bias further comprises a magnetic field provided by a pair of opposing hard magnets located near said upper surface.

17. The bead detector described in claim 14 wherein said conductive stripes run below the sensor in the X direction and wherein each of said stripes has an outer edge that runs in the X direction and is in alignment with an outer edge of said detector.

18. The bead detector described in claim 17 wherein said magnetic bias further comprises a magnetic field provided by a pair of opposing hard magnets located near said upper surface.

19. The bead detector described in claim 14 wherein said conductive stripes further comprise:
a first pair of opposing stripes running in the X direction, optionally overlapped by said sensor, and having a near end and a far end;
a stripe running in the Y direction that connects together said stripes at said far end;
a second pair of stripes, running in the Y direction that connect to said stripes at said near end, said pair of stripes being directed towards each another, and terminating at a non-conductive gap located between said second pair of stripes; and
a third pair of stripes, directed in the X direction away from said sensor and connected to said second pair of stripes on opposing sides of said non-conductive gap, whereby said first, second, and third pairs of stripes together constitute a magnetic coil having an outer boundary, said bead being located within said outer boundary.

20. The magnetic bead detector described in claim 19 wherein said magnetic coil has one or more turns.

21. The magnetic bead detector described in claim 20 wherein said X and Y directions are orthogonal.

22. A magnetic bead detector, comprising:
a free layer having a length that runs in a Y direction and a width that runs in an orthogonal X direction;
a Z direction orthogonal to both X and Y directions;
said detector being constructed to signal the presence of a magnetic field through a change in said free layer's electrical resistance;
said detector having an upper surface that is parallel to said free layer;
a static magnetic field, having a value of between about 1 and 1,000 Oe, in the Y direction;
said free layer being magnetized in the Y direction by said static magnetic field, thereby giving a magnetic bias to said free layer;
said magnetic bead being attached to said upper surface at a binding site; and
external means for generating an alternating magnetic field, in the Z direction, whose frequency is greater than or equal to about 1 MHz.

* * * * *